(12) United States Patent
Suh et al.

(10) Patent No.: US 7,732,203 B2
(45) Date of Patent: Jun. 8, 2010

(54) METHOD FOR TRANSDIFFERENTIATING MESENCHYMAL STEM CELLS INTO NEURONAL CELLS

(75) Inventors: Hae-Young Suh, Suwon-si (KR); Sung-Soo Kim, Seoul (KR); Ji-Won Kim, Suwon-si (KR); Young-Don Lee, Suwon-si (KR); Seung-Cheol Ahn, Seoul (KR)

(73) Assignee: Ajoll University Industry Cooperation Foundation (KR)

( * ) Notice: Subject to any disclaimer, the term of this patent is extended or adjusted under 35 U.S.C. 154(b) by 1411 days.

(21) Appl. No.: 10/525,679

(22) PCT Filed: Aug. 14, 2003

(86) PCT No.: PCT/KR03/01641

§ 371 (c)(1),
(2), (4) Date: Feb. 17, 2005

(87) PCT Pub. No.: WO2004/016779

PCT Pub. Date: Feb. 26, 2004

(65) Prior Publication Data

US 2006/0099190 A1    May 11, 2006

(30) Foreign Application Priority Data

Aug. 17, 2002  (KR) .................. 10-2002-0048683

(51) Int. Cl.
*A61K 48/00* (2006.01)
*C12N 15/00* (2006.01)
*C12N 5/08* (2006.01)
*C12N 5/00* (2006.01)
*C12N 5/02* (2006.01)

(52) U.S. Cl. .................. 435/377; 435/455; 435/368; 424/93.2

(58) Field of Classification Search .......... 424/93.2; 435/455
See application file for complete search history.

(56) References Cited

U.S. PATENT DOCUMENTS 7,547,545 B2 *  6/2009  Prockop et al. ............. 435/373

OTHER PUBLICATIONS

Yoshida et al., 2001, Biochem. J., vol. 360, pp. 683-689.*
Sanchez-Ramos et al. (2000, Exp. Neurology, vol. 164, pp. 247-256).*
Inoue et al. (2001, Genes to Cells, vol. 6, pp. 977-986).*
Elwood et al. (1998, Blood, vol. 91, pp. 3756-3765).*
Woodbury et al., 2000, J. Neuroscience Res., vol. 61, pp. 364-370.*
Guillemot F., 1999, Experimental Cell Res., vol. 253, pp. 357-364.*
Zou et al., 2002, J. Neuroscience, vol. 22(12), pp. 4833-4841.*
Elwood et al., 1998, Blood, vol. 91, pp. 3756-3765.*
1 page printout from medterms.com.*
Exhibit 1: Phinney and Prockop, Stem Cells, 25:2896-2902, 2007.
Exhibit 2: Wiese et al, Cellular and Molecular Life Sciences, 61:2510-2522, 2004.
Exhibit 3: Tondreau et al, Differentiation, 72:319-326, 2004.
Exhibit 4: Lu et al., J. Neurosci, Res., 77:174-191, 2004.
Exhibit 5: Neuhuber et al., J. Neurosci, Re., 77:192-204, 2004.

* cited by examiner

*Primary Examiner*—Peter Paras, Jr.
*Assistant Examiner*—David Montanari
(74) *Attorney, Agent, or Firm*—Baker & Hostetler, LLP

(57) ABSTRACT

This inventive discloses a method for transdifferentiating mesenchymal stem cells into neuronal cells, which comprises increasing the level of a basic helix-loop-helix (bHLH) transcription factor in the mesenchymal stem cells, said cells being useful in cell therapy or gene therapy for treating brain neurological diseases such as Parkinson's disease, Alzheimer disease, Hungtington's disease, amyotrophic lateral sclerosis, cerebral paralysis and brain ischemia; and spine disfunction caused by a traumatic injury.

5 Claims, 8 Drawing Sheets

(A)

(B)

SEQUENCE LISTING

```
<160> NUMBER OF SEQ ID NOS: 2

<210> SEQ ID NO 1
<211> LENGTH: 19
<212> TYPE: DNA
<213> ORGANISM: Artificial Sequence
<220> FEATURE:
<223> OTHER INFORMATION: primer of Neurogenin 1

<400> SEQUENCE: 1
```

```
tgcaagatcc tgccccttt                                                    19
```

```
<210> SEQ ID NO 2
<211> LENGTH: 21
<212> TYPE: DNA
<213> ORGANISM: Artificial Sequence
<220> FEATURE:
<223> OTHER INFORMATION: primer for neurogenin 1

<400> SEQUENCE: 2 tctaccccttt ctggctgaag c                                                21
```

METHOD FOR TRANSDIFFERENTIATING MESENCHYMAL STEM CELLS INTO NEURONAL CELLS

The present application is a U.S. National Stage Application of PCT/KR03/01641, filed on Aug. 14, 2003, which claims priority to Korean Application No. 10-2002-0048683, filed on Aug. 17, 2002.

FIELD OF THE INVENTION

The present invention relates to a method for transdifferentiating mesenchymal stem cells into neuronal cells and a pharmaceutical composition containing the neuronal cells for cell therapy of neurological diseases.

BACKGROUND OF THE INVENTION

Mesenchymal stem cells (MSCs) are multipotent bone marrow stromal cells aiding hematopoiesis and can differentiate into mesodermal lineage cells such as osteocytes, chondrocytes, adipocytes and myocytes. Thus, they can be utilized as sourced for the development of artificial tissues.

It has recently been reported that MSCs have a potential to differentiate into neuroglia in the brain (Azizi., et al., *Proc. Natl. Acad. Sci.* USA, 94, 4080-4085(1998); and Kopen., et. al., *Proc. Natl. Acad. Sci.* USA, 96, 10711-10716(1999)), and therefore, it has been proposed the MSCs can be utilized as sources for the treatment of neurological diseases in the central nervous system (Li et al., *Neurosci. Lett.,* 315, 67-70 (2001); and Chen., et al., *Stroke,* 32, 1005-1011(2001)).

Several growth factors or hormones have been known to induce differentiation of MSCs into neuron like cells. However, those methods have the problem of highly producing non-neuronal cells together with neuronal cells (Sanchez-Ramos., et al., *Exp. Neurol.,* 164, 247-256(2000); Woodbury., et al., *J. Neurosci. Res.,* 61, 364-370(2000); and Deng., et al., *Biochem. Biophys. Res. Comm.,* 282, 148-152(2001)). The problem is more pronounced when the cells are transplanted into the brain of experimental animals (Azizi., et al., *Proc. Natl. Acad. Sci.* USA, 94, 4080-4085(1998); and Kopen., et al., *Proc. Natl. Acad. Sci.* USA, 96, 10711-10716(1999)).

Thus, there has existed a need to develop a novel method for higher induction of MSCs into neuronal cells.

Neurogenin and neuroD are the basic helix-loop-helix (bHLH) transcription factors which play important roles in the formation of the nervous system. They form heterodimers with other bHLH transcription factors, such as E12 or E47 and bind to DNAs containing E-box (CANNTG), or on rare occasions, DNAs containing N-box. Such binding to DNA has been reported to be an essential step for the bHLH transcription factors to induce expression of tissue-specific genes (Lee, *Curr. Opni. Genet. Dev.,* 7, 13-20(1997)).

The present inventors have endeavored to develop an effective method for transdifferentiating MSCs into neuronal cells; and have unexpectedly found that MSCs transduced with bHLH transcription factors such as neurogenin and neuroD can continuously express the bHLH transcription factors; and that the MSCs expressing the bHLH transcription factors can be transdifferentiated into a high level of neuronal cells when MSCs are transplanted into the brain of experimental animals.

SUMMARY OF THE INVENTION

Accordingly, it is a primary object of the present invention to provide a method for transdifferentiating mesenchymal stem cells into neuronal cells.

It is another object of the present invention to provide a pharmaceutical composition for cell therapy of neurological diseases.

It is still another object of the present invention to provide a kit for transdifferentiation of the mesenchymal stem cells into neuronal cells.

In accordance with one aspect of the present invention, there is provided a method for transdifferentiating mesenchymal stem cells into neuronal cells, which comprises increasing the level of neurogenic basic Helix-Loop-Helix (bHLH) transcription factors in the mesenchymal stem cells.

In accordance with another aspect of the present invention, there is provided a pharmaceutical composition for cell therapy of neurological diseases, which comprises a therapeutically effective amount of MSCs transduced with neurogenic bHLH transcription factors or neuronal cells transdifferentiated therefrom.

In accordance with still another aspect of the present invention, there is provided a kit for transdifferentiation of mesenchymal stem cells into neuronal cells, which comprises expression vectors containing genes encoding neurogenic bHLH transcription factors or active fragments thereof.

BRIEF DESCRIPTION OF THE DRAWINGS

The above and other objects and features of the present invention will become clear from the following description of the invention taken in conjunction with the following accompanying drawings, which respectively show.

DETAILED DESCRIPTION OF THE INVENTION

Figure 1:
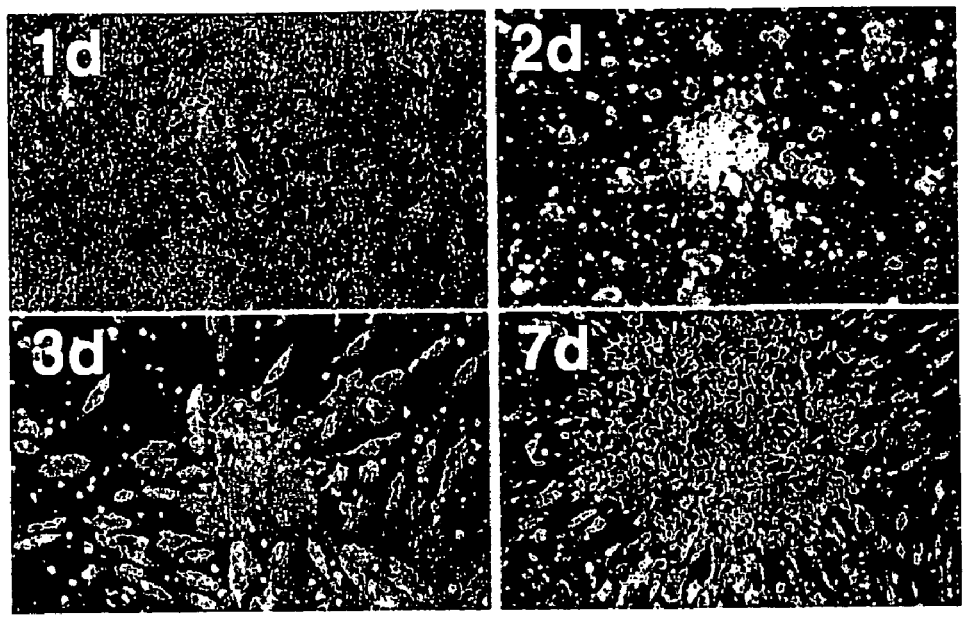
FIG. 1: light microscopic photographs of mesenchymal stem cells isolated from human bone marrow after cultivating for 1, 2, 3, and 7 days in vitro.

In the present invention, the cDNAs of bHLH transcription factors can be prepared by cloning or synthesizing based on the sequence information, including neurogenin 1 gene (Genbank Accession No.: U63842, U67776), neurogenin 2 gene (Genbank Accession No.: U76207, AF303001), neuro D1 gene (Genbank Accession No.: U24679, AB018693), MASH1 gene (Genbank Accession No.: M95603, L08424), MATH3 gene (Genbank Accession No.: D85845) and E47 gene (Genbank Accession No.: M65214, AF352579) in accordance with a conventional method well known in the art. Further, the neurogenic transcription factors which may be used in the present invention include those genes modified by changing, deleting or substituting portion of the genes without any substantial change of the activity of said genes.

The mesenchymal stem cells which may be used in the present invention can be isolated from the bone marrow, peripheral blood and cord blood of any mammal including human, preferably from the human bone marrow, wherein the age of the mammal does not limit the scope of the invention.

In order to increase the level of bHLH transcription factors in MSCs, it is preferred to transduce bHLH transcription factors into the MSCs directly, or using a suitable carrier, and it is most preferred to transduce a gene encoding a bHLH transcription factor or an active fragment thereof into the MSCs.

For introducing a bHLH transcription factor or an active gene fragment thereof into MSCs, the methods known in the art such as DNA-calcium precipitation method, the method using liposome or polyamines, electroporation and the method using retrovirus or adenovirus can be used. Especially, the method using retrovirus is preferred, and the bHLH transcription factor of the present invention can be transduced by a process which comprises the steps of inserting the cDNA of a bHLH transcription factor into a retroviral vector to obtain an expression vector, transforming a packaging cell with said expression vector, culturing the transformed cell under an appropriate culture condition, filtering the culture medium to obtain a retroviral solution and transducing MSCs with the retroviral solution. Then, MSCs which continuously express bHLH transcription factors can be prepared by using a selection marker present in the retroviral vector.

The MSCs transduced with the bHLH transcription factor of the present invention can differentiate to neuronal cells while inhibiting as osteogenic, chondrogenic, adipogenic and myogenic differentiation. Therefore, MSCs can be differentiated into neuronal cells under a special in vitro condition and transdifferentiated into neuronal cells when the MSCs is transplanted into the brain of experimental animals. Conversion of the mesodermal potential into neural lineages can be confirmed by conducting in vitro experiments. For example, treatment of MSCs with forskolin and/or 5-aza-deoxycytidin facilitate transdifferentiation of MSCs into neuronal cells.

In particular, in order to enhance the neuronal differentiation of MSC, it is preferred to add forskolin to MSCs to a final concentration of 10 to 30 μmol/l, and it is most preferred to pre-incubate MSCs with 5 to 30 μmol/l of 5-aza-deoxycytidin for 3 to 10 days before adding forskolin.

Furthermore, the transdifferentiation efficiency can be increased by adding N2 supplement (Gibco) to the culture medium, preferably, the N2 supplement diluted 100 fold.

By conducting immunohistochemical analysis employing MAP2 (microtubul-associated protein 2), NF200 (neurofilament 200), or NeuN (neuronal nuclei) as a neuronal maker, it can be confirmed that the MSCs expressing bHLH transcription factors transplanted into the striatum of the experimental rats have transdifferentiated into neuronal cells to a much higher degree than MSCs which do not express transcription factors.

The MSCs transduced with a bHLH transcription factor or neuronal cells transdifferentiated therefrom can be used as an active ingredient of a pharmaceutical composition for cell therapy or gene therapy of neurological diseases such as Parkinson's disease, Alzheimer disease, Huntington's disease, amyotrophic lateral sclerosis, cerebral paralysis and brain ischemia; or for therapy of spine disfunction caused by an injury.

The neuronal cells which may be used in the pharmaceutical composition can be prepared by transducing one or more bHLH transcription factors into MSCs, propagating, and differentiating MSCs under a suitable condition in vitro; or by progating MSCs, transducing a bHLH transcription factor into MSCs and differentiating transduced MSCs with a bHLH transcription factor.

For example, the desired gene for gene therapy of a specific brain disease (for example, the tyrosin hydroxylase gene involved in a synthesis of dopamine) can be introduced into the neurological system of an animal by transducing the viral vectors containing the desired gene into MSCs or the neuronal cells transdifferentiated therefrom, and transplanting the cells thus obtained into the brain of the animal. Therefore, the neuronal cells transdifferentiated from MSCs of the present invention can be used as a useful tool for delivering beneficial genes into the nervous system.

A pharmaceutical composition comprising the neuronal cells as an active ingredient can be injected into the patient's body according to the conventional methods well known in the art such as the clinical method disclosed in the open literature (Bjorklund and Stenevi, *Brain Res.*, 177, 555-560 (1979) and Lindvall et al., *Arch. Neurol*, 46, 615-31(1989)).

The unit dose of the neuronal cells of the present invention to be actually administered ought to be determined in light of various relevant factors including the disease to be treated, the severity of the patient's symptom, the chosen route of administration, and the age, sex and body weight of the individual patient.

Moreover, the present invention also provides a kit for neuronal differentiation of MSCs, which comprises the expression vector containing a bHLH transcription factor or an active fragment thereof.

The bHLH transcription factor which may be used in the present invention includes neurogenin 1, neurogenin 2, neuroD, MASH1, MATH3, E47 and an active fragment thereof; and the vector is preferably derived from retrovirus or adenovirus. The kit of the present invention may further comprise forskoline and/or 5-aza-deoxycytidin.

The following Examples are intended to further illustrate the present invention without limiting its scope; and the experimental methods used in the present invention can be practiced in accordance with Examples given herein below, unless otherwise stated.

Example 1

Isolation and Culture of Mesenchymal Stem Cell (Step 1) Extraction of Bone Marrow and Isolation of Mesenchymal Stem Cells 4 ml of HISTOPAQUE 1077 (Sigma) and 4 ml of bone marrow obtained from Bone marrow bank (Korean Marrow Donor Program, KMDP) were added to a sterilized 5 ml test-tube. After centrifugation at 400×g for 30 minutes, 0.5 ml of the buffy coat located in the interphase was collected and transferred into a test-tube containing 10 ml of sterilized phosphate buffered saline. The resulting suspension was centrifuged at 250×g for 10 minutes to remove the supernatant and 10 ml of phosphate buffer was added thereto to obtain a suspension, which was centrifuged at 250×g for 10 minutes. The above procedure was repeated twice and DMEM medium (Gibco) containing 10% FBS (Gibco) was added to the resulting precipitate. A portion of the resulting solution corresponding to $1\times10^7$ cells was placed in a 100 mm dish and incubated at 37° C. for 4 hours while supplying 5% $CO_2$ and 95% air. The supernatant was then removed and a new medium was added to continue culturing.

(Step 2) Culture and Subculture of MSCs

The MSCs obtained in Step 1 were incubated using an MSC medium (10% FBS (Gibco)+10 ng/ml of bFGF (Sigma)+1% penicillin/streptomycin (Gibco)+89% DMEM (Gibco)) in a $CO_2$ incubator kept at 37° C. Serial incubations were carried out while changing the medium at an interval of 2 days. When the cells reached to 80% confluence, the cells were collected using 0.25% trypsin/0.1 mM EDTA (Gibco) and diluted 20 fold with the medium, and then, subcultured in the new dishes. The rest of cells thus obtained were kept frozen in a medium containing 10% DMSO (Sigma). FIG. 1 shows light microscopic photographs of mesenchymal stem cells isolated from human bone marrow after cultivating for 1, 2, 3, and 7 days in vitro.

(Step 3) Multiple Differentiation Potentials of MSCs

In vitro differentiation potentials of MSCs into adipocytes, chondrocytes and osteocytes were examined as follows.

1) Adipogenic Differentiation of hMSCs

Figure 2:
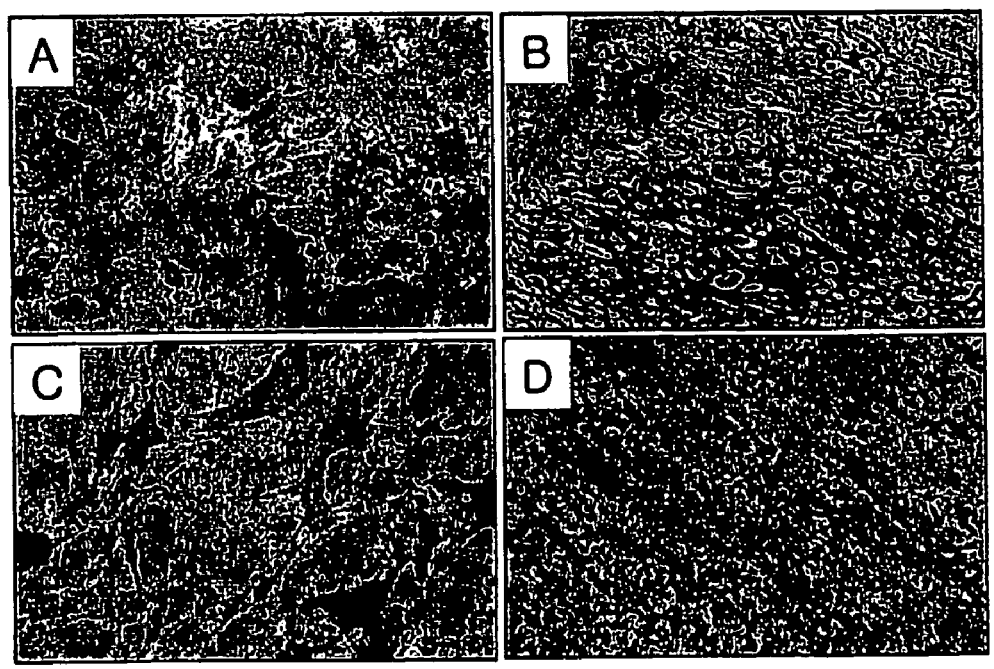
FIGS. 2A to 2D: photographs showing multi-potentials of MSCs (A: adipocytes stained with oil red-O; B: chondrocytes stained with alcian blue; C: alkaline phosphatase activity in osteocytes; and D: osteocytes stained with von Kossa.

MSCs were cultured in the MSC medium, followed by culturing in an adipogenic differentiation induction medium (DMEM medium (Gibco) supplemented with 1 μM dexamethasone (Sigma), 0.5 mM methylisobutylxanthine (Sigma), 10 μg/ml of insulin (Gibco), 100 nM indomethacin (Sigma) and 10% FBS (Gibco)) for 48 hours. The resulting mixture was subsequently incubated in an adipogenic maintenance medium (DMEM medium containing 10 μg/ml of insuline and 10% FBS) for 1 week and stained with oil red O. As shown in FIG. 2, adipocytes stained with oil red O is pronounced inside the cells. This result suggests that MSCs can be successfully differentiated into adipocytes.

2) Chondrogenic Differentiation of MSCs

MSCs were cultured in the MSC medium. $2\times10^5$ of the cells were collected using trypsin, centrifuged, and then, re-incubated in 0.5 ml of a serum-free chondrogenic differentiation induction medium (50 ml of high-glucose DMEM (Gibco) containing 0.5 ml of 100×ITS (0.5 mg/ml of bovine insulin, 0.5 mg/ml of human transferrin, 0.5 μg/ml of sodium selenate (Sigma) and 10 ng/ml of TGF-β1(Sigma)) for 3 weeks while replacing the medium every 3 days. Then, the cell masses were fixed with 4% paraformaldehyde, sectioned using a microtome, and then, stained with alcian blue (FIG. 2B). As shown in FIG. 2B, the extracellular cartilage matrix was stained blue and the presence of chondrocytes in cartilage lacunae was observed. These results suggest that the MSCs were differentiated into chondrocytes.

3) Osteogenic Differentiation of hMSCs

MSCs were incubated in the MSC medium, followed by culturing in 0.5 ml of an osteogenic differentiation induction medium (DMEM supplemented with 10 mM β-glycerol phosphate (Sigma), 0.2 mM ascorvate-2-phosphate (Sigma), 10 nM dexamethasone (Sigma) and 10% FBS (Gibco)) for 2 weeks while replacing the medium every 3 days. Then, the cells were fixed with 4% paraformaldehyde and stained for alkaline phosphatase and and with von Kossa method. As shown in FIGS. 2C and 2D, the increase of the alkaline phosphatase activity and the extracellular accumulation of calcium minerals in the form of hydroxyapatite suggest that the MSCs were differentiated into osteocytes.

Example 2

Construction of a Retroviral Vector Expressing Neurogenin 1, a Neurogenic Transcription Factor (Step 1) Construction of Retroviral Vector Expressing Neurogenin 1 (ngn1)

Figures 3, 4:
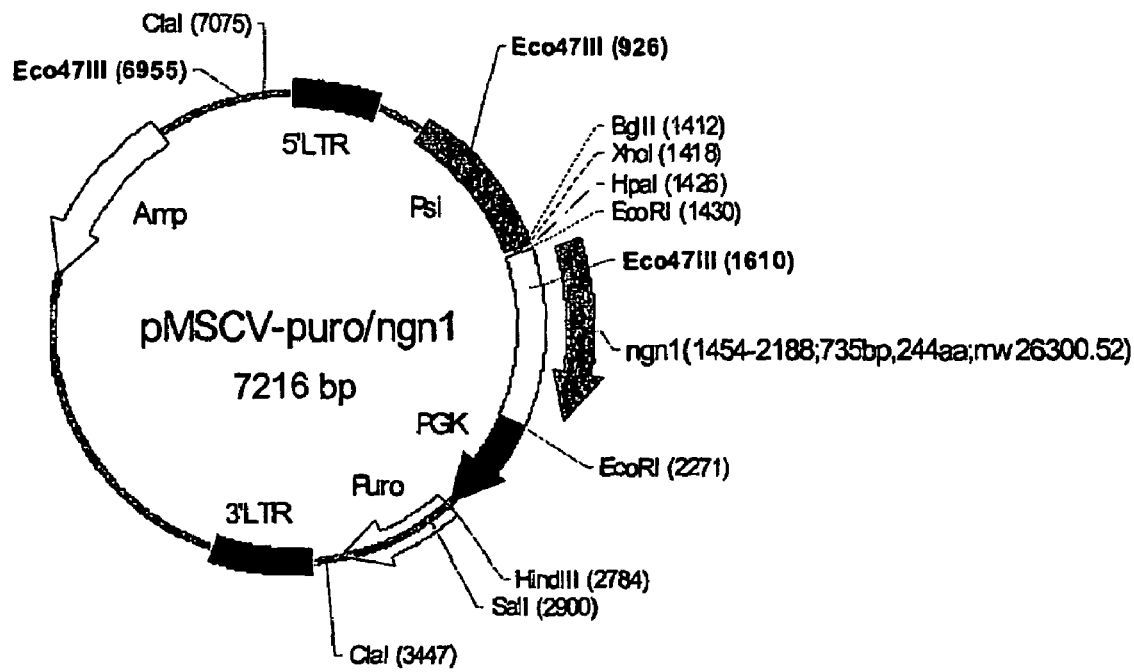
FIG. 3: the construction of a retrovirus vector which expresses neurogenin1 (ngn1), a neurogenic transcription factor.
FIG. 4: western blotting analysis showing expression of ngn1 in the cytoplasm and nucleus of 293T cells transfected with a retroviral plasdmid encoding the ngn1 gene.

PCR was carried out using oligonucleotides of SEQ ID NOS.: 1 and 2 as primers and genomic DNA of Balb/c mouse as a template, and the PCR product thus obtained was cloned using TOPO TA cloning kit (Invitrogen). Through sequence analysis of the vector cloned, it was confirmed that the vector contained neurogenin 1 gene. The neurogenin 1 cDNA was isolated with EcoRI and inserted into the EcoRI site of vector pMSCV-puro (Clontech, USA) with T4 DNA ligase (Roche) and transformed into *E. coli* DH5α to obtain pMSCV-puro/ngn1. The resulting construct of pMSCV-puro/ngn1 is shown in FIG. 3.

(Step 2) Expression of Neurogenin1 Retroviral Vector pMSCV-puro/ngn1 vector was transfected into 293T/17 cell (ATCC CRL-11268) according to the calcium phosphate-coprecipitation method. After 48 hours of transduction, the cell was fractionated into cytoplasm and nucleus. In order to confirm the expression of neurogenin1, each fraction was subjected to western blot analysis using anti-neurogenin1 antibody (Chemicon). As shown in FIG. 4, neurogenin1 protein was expressed in the nuclear fraction of 293T/17 cell transfected with the pMSCV-puro/ngn1 vector.

(Step 3) Preparation of Retrovirus Containing Neurogenin1 pMSCV-puro/ngn1 vector was transfected into retroviral packaging cell lines, PA317 (ATCC CRL-9078) or PG13 (ATCC CRL-10686) according to the calcium phosphate-coprecipitation method. After 48 hours of transduction, the culture solution was collected and filtered with 0.45 μm membrane to Zobtain retrovirus solution. The retrovirus solution was kept at −70° C. until use.

Example 3

Transduction of Neurogenin1 into MSCs

Figures 5, 6:
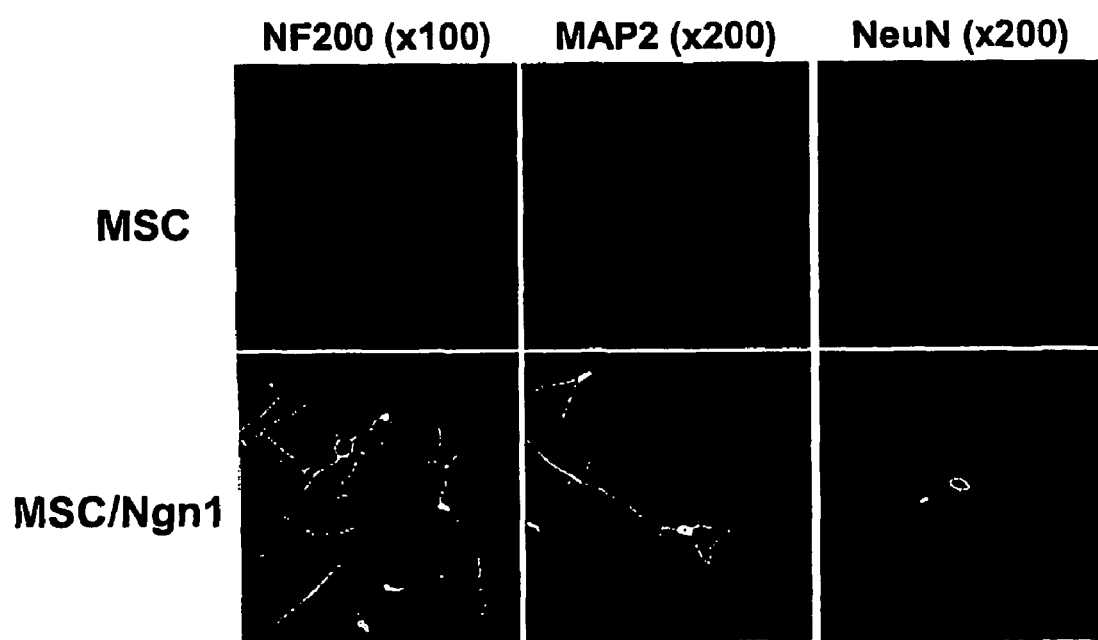
FIG. 5: western blotting analysis showing expression of ngn1 in the cytoplasm and nucleus of MSCs transduced with a retroviral vector encoding the ngn1 gene.
FIG. 6: in vitro immunocytochemical staining showing neuronal differentiation of MSCs transduced with a retroviral vector encoding ngn1 using antibodies against NF200 (neurofilament 200), MAP2 (microtubul-associated protein 2) and NeuN (neuronal nuclei) as neuronal markers.

MSCs were cultured to 70% confluence in 100 mm dishes. Added thereto was 4 ml of the retrovirus solution obtained in Example 2 which was mixed with polybrene (Sigma) to a final concentration of 8 μg/ml and incubated for 8 hours. The retrovirus solution was then removed, the MSCs were cultured in 10 ml of MSC medium for 24 hours. The above procedure was repeated 1-4 times. Then, MSCs were collected using trypsin and diluted 20 fold with the medium. The obtained cells were subcultured in a medium supplemented with 2 μg/ml of puromycin (Sigma) for 2 weeks. The puromycin positive cells were fractionated into cytoplasm and nucleus. In order to confirm the expression of neurogenin1, each fraction was subjected to western blot analysis using anti-neurogenin1 antibody. The result is shown in FIG. 5. As can be seen in FIG. 5, neurogenin1 protein was expressed in the nucleus of MSCs transduced with Ngn1 gene.

Example 4

In Vitro Neuronal Differentiation of MSCs Expressing Neurogenin1

(Step 1) Induction of Neuronal Differentiation

In order to induce in vitro neuronal differentiation of MSCs expressing neurogenin1 (MSC/Ngn1), $5 \times 10^3$ of the MSCs were plated on a cover-glass of 12 mm diameter coated with a mixture of poly-D-lysine and collagen (0.1 mg/ml each). Then, the cells was cultured in MSC medium supplemented with 10 μg/ml of 5-aza-deoxycytidine (Sigma) for 3 to 7 days, followed by culturing in F12/DMEM supplemented with 10 μM of forskolin and N2 supplement (100×, Gibco) for 1 week.

(Step 2) Immunocytochemistry

To examine neuronal differentiation of MSC/Ngn1, immunocytochemistry was carried out as follows.

Anti-MAP2 monoclonal antibody (Sigma, 1:200), Anti-NF200 polyclonal antibody (Sigma, 1:400) or Anti-NeuN monoclonal (Chemicon, 1:100) was used as a primary antibody, and a fluorescence-labeled, as a secondary antibody to detect the primary antibody according to the manufacturers' guidelines.

Cells were washed with PBS and fixed with 4% paraformaldehyde at room temperature for 20 min. The fixed cells were washed three times with PBS and blocked with PBS containing 10% normal horse serum and 0.1% triton X-100 at room temperature for 2 hours. The cells thus obtained were reacted with the primary antibody overnight at 4° C. in PBS containing 10% normal horse serum, and washed three times with PBS containing 0.1% Triton X-100 10 minutes each. The cells were added with the secondary antibody in PBS at room temperature for 1 hour and washed three times with PBS containing 0.1% Triton X-100 each for 10 minutes.

The result is shown in FIG. 6. As can be seen in FIG. 6, MSC/Ngn1 outgrew long neurites which were stained with antibodies against neurite specific proteins, NF200 and MAP2. In addition, the cells were also immunoreactive to an antibody against neuronal nucleus specific NeuN antibody.

(Step 3) Electrophyiological Recording

To examine functional maturation of the transdifferentiated neuronal cells, electrophysiological recording for the neuronal cell was carried out as follows.

The electric current of the cell membrane was amplified using an axopatch-1C patch-clamp amplifier (Axon Instrument, U.S.A.) and current signals were filtered at 5 kHz to be displayed on an oscilloscope (20 MHz digital storage, type 1425, Gould, U.S.A.). The obtained current traces were analyzed with Clampfit v. 6.0.3. Physiological salt solution (PSS) was composed of 150 mM NaCl, 5 mM KCl, 1.5 mM $CaCl_2$, 1 mM $MgCl_2$, 5 mM glucose and 10 mM HEPES (N-(2-hydroxyethyl) piperazine N-(2-ethanesulfonic acid)). The pH of the physiological salt solution was adjusted to 7.4 using NaOH and kept at 36° C. Patch pipette was adjusted to 3-4 MΩ and a Cs-rich pipette solution (consisting of 90 mM Cs-aspartate, 55 mM CsCl, 3 mM $Na_2ATP$, 3 mM $Na_2$-creatine phosphate, 1 mM $MgCl_2$, 10 mM HEPES, 10 mM EGTA, pH 7.4) was employed.

Figure 7:
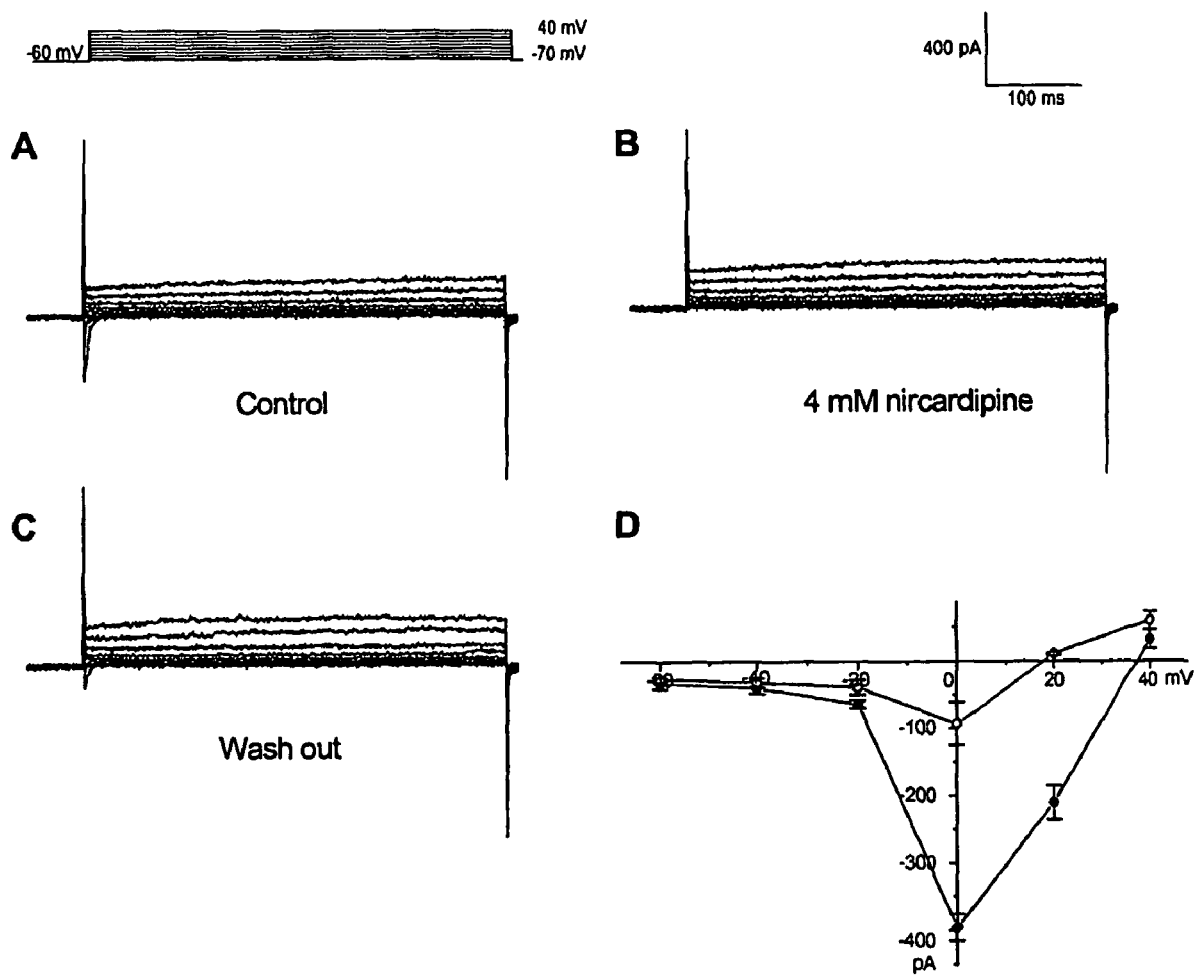
FIG. 7: in vitro electrophyiological recordings showing that MSCs transduced with a retroviral vector encoding the ngn1 gene acquired a neuronal phenotype.

The result is shown in FIG. 7. As can be seen in FIG. 7, an inward current was detected in 16 cells out of 27 MSC/Ngn1 cells (FIG. 7A). The inward current was selectively blocked by 4 μM nicardipine which is an L-type $Ca^{2+}$ channel blocker (FIG. 7B) and recovered by the removal of nicardipine (FIG. 7C). The current-voltage relation exhibited a bell shape typical of the voltage dependent L-type Ca2+ channel (FIG. 7D) but no current was measured in MSC/lacZ cells. The results suggest that Ngn1 induces the functional maturation of the neuronal cells by inducting the electrophysiological properties of human MSCs.

Example 5

In Vitro Neuronal Differentiation of MSCs Co-Expressing Neurogenin1 and E47 or NeuroD1 and E47

To examine the effect the NeuroD1 gene, the neurogenin1 component of the expression vector obtained in Example 2 was replaced with NeuroD1 gene (Genbank Accession No.: U67776) and E47 (Genbank Accession No.: AF352579) to obtain NeuroD1 and E47 expression vectors, respectively. Mixtures of 4 μg of neurogenin1 expression vector+1 μg of E47 expression vector, or 4 μg of NeuroD1 expression vector+1 μg of E47 expression vector were mixed with 16 μl of ExGEN500 (MBI Fermenta) and 1 ml of 0.1 mM NaCl solution and added to $2 \times 10^5$ of MSCs. Two hours after transfection, the medium was replaced with fresh MSC medium. Twenty-four hours after the medium was replaced with F12/DMEM supplemented with N2 supplement (100×, Gibco) and waited 2 more days. In order to confirm the expressions of NF200, NF-M and β-tubulin III, neuronal cell markers, the resulting culture was subjected to western blot analysis using anti-NF200 (neurofilament 200, Chemicon), anti-NF-M (neurofilament M, Zymed), and anti-β-tubulin III (BAbCO) antibodies.

Figure 8:
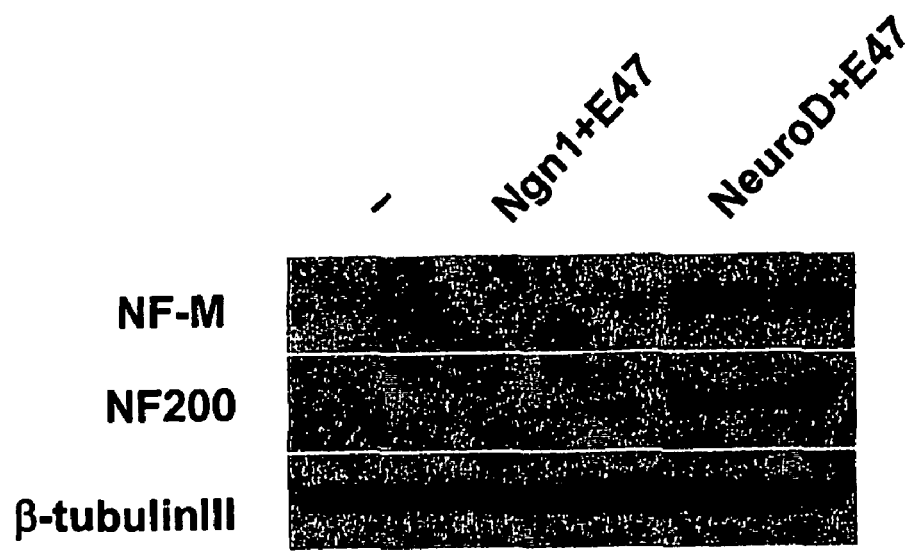
FIG. 8: in vitro western blotting analysis showing neuronal differentiation that MSCs transduced with ngn1/E47 and neuroD/E47 using antibodies against NFM (neurofilament-M), NF200 (neurofilament 200), and β-tubulin III.

The result is shown in the FIG. 8. As shown in the FIG. 8, the expression of NF200 and NF-M proteins increased with the expression of neurogenin1/E47 or NeuroD/E47 in MSCs. The results suggest that the MSCs were transdifferentiated into neuronal cells. However, β-tubulin III was expressed in undifferentiated MSCs, and therefore, it failed to serve as an effective neuronal cell marker.

Example 6

In Vivo Neuronal Differentiation of MSCs Expressing Neurogenin1

(Step 1) Preparation of MSCs for Transplantation.

MSCs expressing neurogenin1 were prepared according to the method of Example 3. In order to examine whether neurogenin1 gene increases the neuronal differentiation of MSCs, MSCs expressing β-galactoxidase (MSC/lacZ), which were to be used as a control, were prepared by carrying out the procedure of Example 2 except that Ngn1 gene was replaced with lacZ gene. Before transplantation, MSCs expressing the lacZ or neurogenin1 gene were pre-stained with Hoechst 33258(Molecular Probe) or transduced with adenovirus carrying the nuclear localizing sequence bound to β-galactoxidase. The Hoechst 33258 pre-staining was carried out by incubating the cells in MSC medium supplemented with 1 μg/ml of Hoechst 33258 (Molecular Probes) for 24 hours. The adenovirus transfection was carried out by adding the adenovirus solution (titer=1×10$^8$ pfu/ml) with 100 m.o.i. (multiplicity of infection) for 3 hours. After pre-staining or transducing, MSCs expressing lacZ or neurogenin1 were collected using 0.25% trypsin/0.1% EDTA (Gibco) and diluted with PBS (Gibco) to 3×10$^3$ cells/μl.

(Step 2) Transplantation

Transplantation was carried out using adult Sprague-Dawley albino rats as follows.

Female Sprague-Dawley albino rats were anesthetized by injecting a 350 mg/kg dose of chlroral hydrate (Sigma), the fur at the incision region was removed, and then, fixed to a stereotaxic frame. The vertex was sterilized with 70% ethanol and the 1 cm incision was made. After drilling at the exposed dura at positions of bregma+1, ML+3 and LV+4, 1 μl of PBS containing 3×10$^3$ cells of MSC/lacZ or MSC/Ngn1 was injected at a rate of 0.2 μl/min using a Hamilton syringe. Twenty minutes after injection, the syringe was removed. The incision was sutured. Cyclosporin A (Sigma), an immunosuppressant, was daily administed (5 mg/kg) by intraperitoneal injection until the brain was extracted.

(Step 3) Preparation of Tissue Slice

Two and six weeks after transplantation, the rats were anesthetized by injecting 400 mg/kg of chloral hydrate (Sigma). The rats were perfused with PBS and then with 0.1 M paraformaldehyde in PBS (pH 7.4). The brain was extracted and kept at 4° C. in 0.1 M paraformaldehyde in PBS (pH 7.4) for 16 hours to post-fix. The post-fixed brain was deposited in 30% sucrose for 24 hours and sectioned using a sliding microtome with a thickness of 35 μm. The sections thus obtained were mounted to silane-coated slides (MUTO PUREW CHEMICAS CO., LTD, Japan) and stored at 4° C. in PBS till use.

FIG. 8 is a fluorescent microscopic photograph showing the integration rate of transplanted MSCs expressing lacZ or neurogenin1 gene in the striatum of the rats two weeks after transplantation. The graft efficiency is shown in Table 1.

TABLE 1

|  | Graft efficiency (%) |
| --- | --- |
| MSC | 45 |
| MSC/Ngn1 | 54 |

Figure 9:
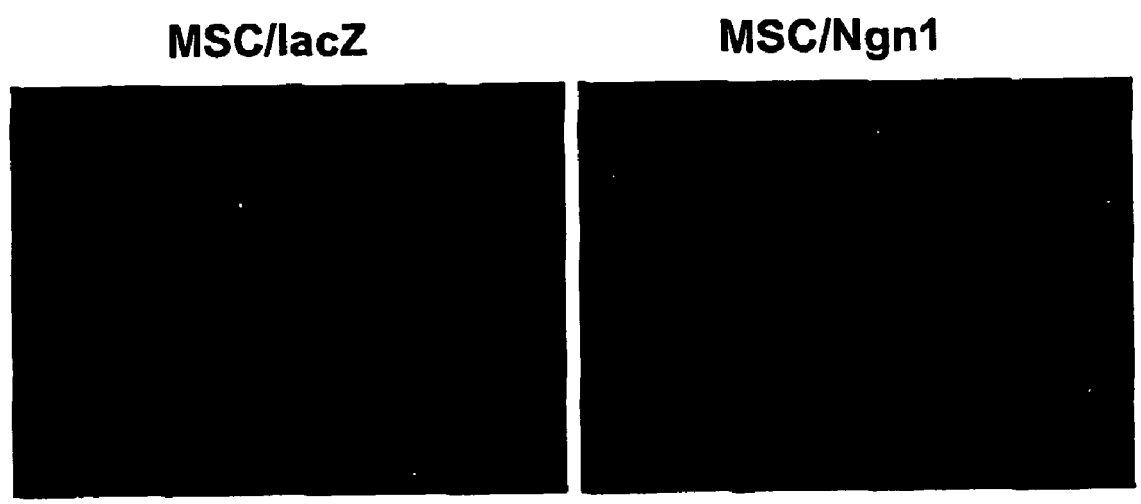
FIG. 9: a fluorescent microscopic photograph showing the integration of MSC/Ngn1 and MSC/lacZ in the rat striatum 2 weeks after transplantation.

As can be seen in FIG. 9 and Table 1, the transplantation rate of MSC/Ngn1 was higher than that of MSC/lacZ. This result suggests that MSC expressing ngn1 was effective for cell therapy.

(Step 4) Immunohistochemistry

The tissue section mounted on a slide was kept in 1×PBS/0.1% tritonX-100 for 30 minutes. To block non-specific interaction, the tissue section was reacted with 10% normal horse serum at room temperature for 1 hour, and then, reacted with a primary antibody at 4° C. for 16 hours. The primary antibodies were anti-NeuN mouse monoclonal antibody (Chemicon, Inc.) (1:200), anti-GFAP mouse monoclonal antibody (Sigma, Inc.) (1:200), anti-human nuclei antibody (Chemicon) (1:50) or anti-human Tau mouse monoclonal antibody (Abcam) (1:100). After washing three times with 1×PBS/0.1% triton X-100 for 15 minutes, the sections were allowed to react with FITC-conjugated anti-mouse IgG (Vector, 1:200) or Taxas red-conjugated anti-mouse IgG (Vector, 1:200) to detect the primary antibody.

In order to further confirm the origin of the cells, a double immunohistochemitry analysis was carried out. The tissue section that were primarily stained with antibodies against NeuN, GFAP, and human nuclei as above and then stained with anti-β-galactosidase rabbit polyclonal antibody (Abcam) (1:500) at room temperature for 2 hours, and then, reacted with Taxas red-conjugated anti-rabbit IgG (Vector, 1:200).

Figure 10:
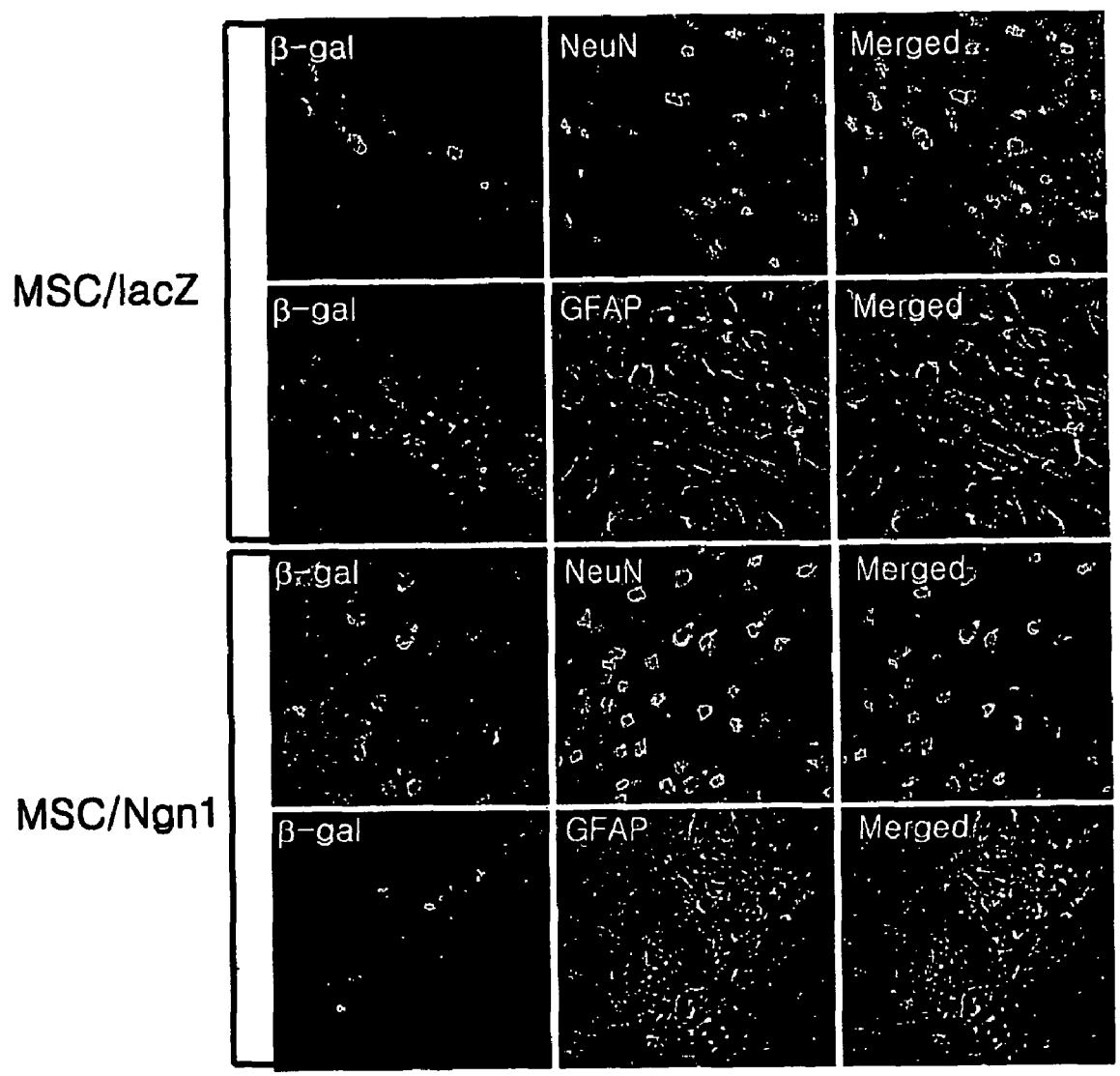
FIG. 10: double immunohistochemical stainings for the colocalization of β-galactosidase either with a neuron specific marker, NeuN, or an astrocyte specific marker, GFAP, in the rat brain 2 weeks after transplantation of MSC/Ngn1 and MSC/lacZ.
Figure 11:
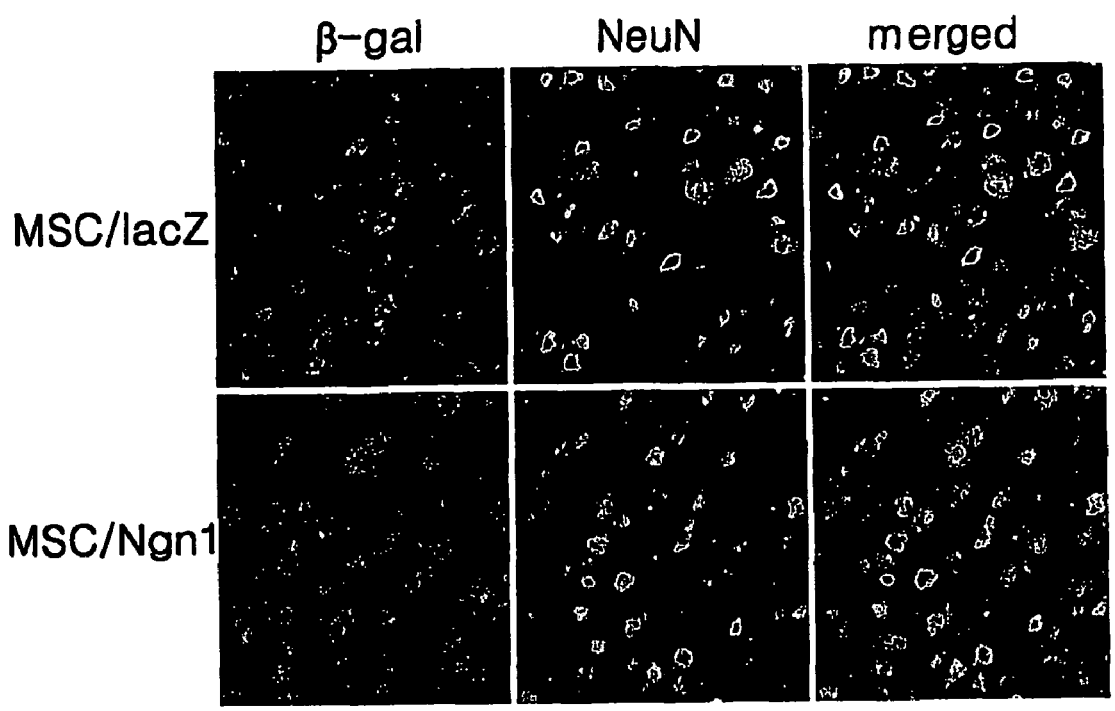
FIG. 11: double immunohistochemical stainings showing expression of β-galactosidase and a neuron specific marker, NeuN in the rat brain 6 weeks after transplantation of MSC/Ngn1 and MSC/lacZ.
Figure 12:
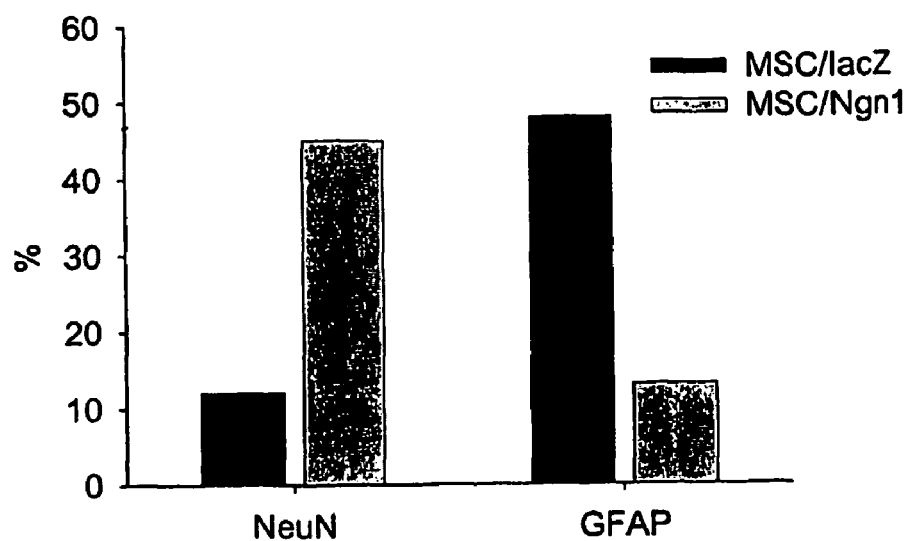
FIG. 12: a graph summarizing the results of FIG. 10.

As can be seen in FIGS. 10 and 11, MSCs expressing neurogenin1 were converted into neuronal cells with higher rates than MSC/lacZ. In case of MSC/lacZ, 45% of the cells were positive for GFAP, a astocytic marker and 12% of the cells were positive for NeuN, a neuronal marker. In contrast, in case of MSC/Ngn1, 13% of the cells were GFAP positive for GFAP, and 48% of the cells were NeuN positive (FIG. 12).

Figure 13:
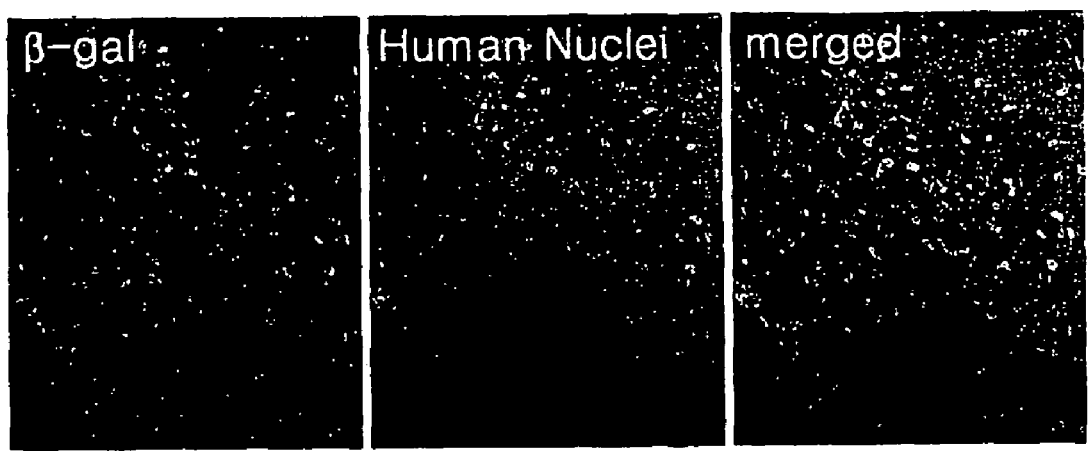
FIG. 13: double immunohistochemical stainings showing colocalization β-galactosidase and Human nuclei in the rat brain 2 weeks after transplantation MSC/Ngn1 (A) and presence of a human specific mature neuronal marker, Tau, using an anti-human Tau antibody (B).
Figure 13:
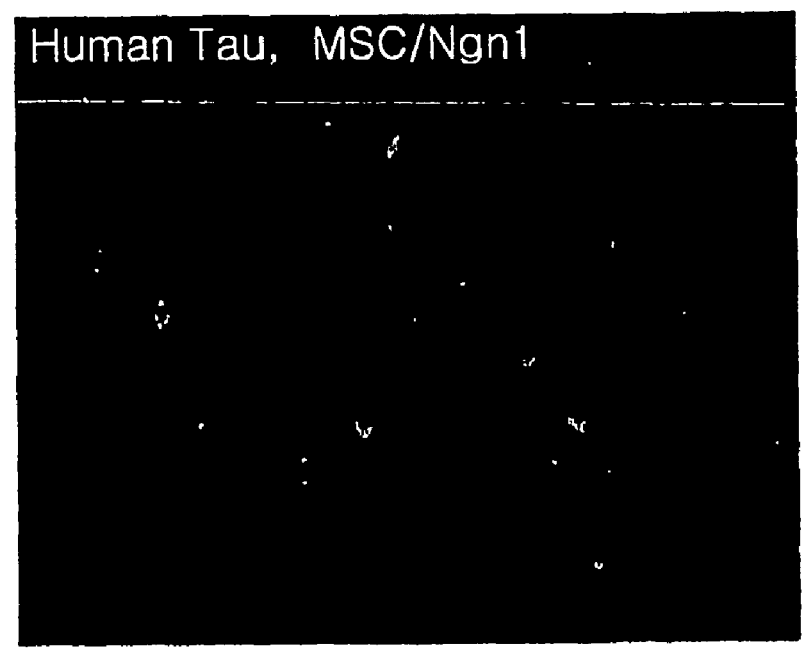

Six weeks after transplantation, MSCs expressing neurogenin1 were also transdifferentiated into NeuN-positive neuronal cells to a higher level than MSC/lacZ (FIG. 11). Through the double immunohistochemistry using anti-human nuclei mouse monoclonal antibody, it was confirmed that the cells reactive to anti-β-galactosidase rabbit polyclonal antibody were originated from the transplanted human cells (FIG. 13A). Furthermore, those cells were also positive for human Tau, a mature human neuronal cell maker. Therefore, it is confirmed that MSCs expressing neurogenin1 were transdifferentiated into mature neuronal cells (FIG. 13B).

This result suggests that the expression of neurogenin1 in MSCs induce the neuronal differentiation while inhibiting astroglial differentiation.

While the invention has been described with respect to the above specific embodiments, it should be recognized that various modifications and changes may be made to the invention by those skilled in the art which also fall within the scope of the invention as defined by the appended claims.

What is claimed is:

1. An in vitro method for transdifferentiating mesenchymal stem cells into neuronal cells, which comprises increasing the level of a basic helix-loop-helix (bHLH) transcription factor in the mesenchymal stem cells by transducing a nucleic acid sequence encoding the bHLH transcription factor and adding 5-aza deoxycitidin and then forskolin, to the mesenchymal stem cells.

2. The method of claim 1, wherein the bHLH transcription factor is selected from the group consisting of neurogenin 1, neurogenin 2, neuro D1, MASH1, MATH3, L47 or a mixture thereof.

3. The method of claim 1, wherein the step of transducing the bHLH transcription factor into the mesenchymal stem cells is conducted by transducing the mesenchymal stem cells with a viral vector encoding the bHLH transcription factor.

4. The method of claim 1, wherein the forskolin is added in an amount of 10 to 30 μmol/l and the 5-aza-deoxycitidin is added in an amount of 5 to 30 μmol/l.

5. The method of claim 1, which comprises culturing the mesenchymal stem cells in a medium supplemented with N2 supplement.

* * * * *